United States Patent [19]

Abrams et al.

[11] Patent Number: 5,034,223
[45] Date of Patent: Jul. 23, 1991

[54] METHODS FOR IMPROVED TARGETING OF ANTIBODY, ANTIBODY FRAGMENTS, HORMONES AND OTHER TARGETING AGENTS, AND CONJUGATES THEREOF

[75] Inventors: Paul G. Abrams, Seattle; Robert W. Schroff; Alton C. Morgan, Jr., both of Edmonds, all of Wash.

[73] Assignee: NeoRx Corporation, Seattle, Wash.

[21] Appl. No.: 107,136

[22] Filed: Oct. 9, 1987

Related U.S. Application Data

[63] Continuation-in-part of Ser. No. 917,176, Oct. 9, 1986, abandoned.

[51] Int. Cl.$^5$ .................. A61K 39/395; A61K 39/44
[52] U.S. Cl. ................ 424/85.8; 424/85.91; 424/1.1; 514/885
[58] Field of Search ............... 424/85.8, 85.91, 1.1

[56] References Cited

U.S. PATENT DOCUMENTS

| | | | |
|---|---|---|---|
| 4,454,106 | 6/1984 | Gansow et al. | 424/1.1 |
| 4,624,846 | 11/1986 | Goldberg | 530/387 |
| 4,676,980 | 1/1987 | Segal et al. | 424/85.8 |
| 4,681,760 | 7/1987 | Fathman | 424/85.8 |
| 4,689,311 | 8/1987 | Weltman | 424/85.8 |
| 4,731,244 | 3/1988 | Talle et al. | 424/87 |
| 4,797,475 | 1/1989 | Terasaki et al. | 530/387 |
| 4,921,690 | 5/1990 | Beatty et al. | 424/1.1 |

OTHER PUBLICATIONS

Tagliahue et al, Hybridoma 5(2) 1986, pp. 107–115.

*Primary Examiner*—Garnette D. Draper
*Attorney, Agent, or Firm*—Seed and Berry

[57] ABSTRACT

Methods for improved targeting of antibody, antibody fragments, peptides hormones, steroid hormones and conjugates thereof are disclosed. Enhanced delivery to target cells of antibodies or fragments thereof or other receptor-mediated delivery system, such as peptide, specific for a population of cells of a mammal comprises steps of administering to said mammal an adequate dosage of blocking antibodies or fragments thereof or other receptor-mediated delivery system, such as peptide, and administering to said mammal an effective dosage of said antibodies or fragments thereof or other receptor-mediated delivery system, such as peptide, specific for said population of cells. In the preferred embodiment, the specific antibodies are monoclonal antibodies directed toward tumor-associated antigen in man.

31 Claims, No Drawings

METHODS FOR IMPROVED TARGETING OF ANTIBODY, ANTIBODY FRAGMENTS, HORMONES AND OTHER TARGETING AGENTS, AND CONJUGATES THEREOF

CROSS-REFERENCE TO RELATED APPLICATION

This application is a continuation-in-part of co-pending application Ser. No. 917,176, filed Oct. 9, 1986 now abandoned.

1. Technical Field

The present invention generally relates to methods for enhancing targeting of antibodies, antibody fragments, peptide hormones and steroid hormones, and conjugates thereof. More specifically, methods are disclosed employing blocking antibodies, fragments, hormones and other targeting agents, and conjugates thereof to reduce cross-reactive and nonspecific binding of specific antibodies, hormones and other targeting agents to non-target cells.

2. Background Art

Antibodies are proteins that have a binding site that is specific for a particular determinant, e.g., antigen or epitope, and other portions that bind to normal tissues in a nonspecific fashion. There are several immunological concepts, all related to antibody binding, that require definition.

Target-specific binding: Binding of the antibody, whole or fragment, hormones, other targeting agents or conjugate thereof, through the antibody's binding site, to the epitope recognized by said antibody on cells expressing said epitope's or hormone's receptor, where said cells are the desired target of the antibody, whole or fragment, or hormone, other targeting agent, or conjugates thereof.

An example of target-specific binding is binding of the antibody, whole or fragment, or conjugate thereof, to tumor cells where the antibody in question can also bind specifically to normal cells. The component of binding to the tumor cells is target-specific. Another example is binding of bombesin, or gastrin-releasing peptide, to small cell lung carcinoma.

Cross-reactive binding: Binding of the antibody, whole or fragment, or hormone, other targeting agent or conjugate thereof, through the antibody's binding site, to the epitope recognized by said antibody on cells expressing said epitope or hormone receptor, where said cells are not the desired target of the antibody, whole or fragment, or hormone or conjugate thereof.

An example of cross-specific binding is binding of the antibody, whole or fragment, or conjugate thereof, to normal lung by antibody binding site to the same or structurally homologous epitope as is present on a tumor cell. The component of binding to the normal lung cells by the antigen-binding site of the antibody is cross-reactive. Another example is the binding of bombesin, or gastrin-releasing peptide, to normal cells in the stomach or pancreas.

Nonspecific binding: Binding of an antibody, whole or fragment, or hormone or conjugate thereof, through some mechanism other than the antigen-recognition binding site of the antibody or hormone, to cells other than the target cells.

An example of nonspecific binding is the uptake of antibody into the liver and spleen due to binding of the antibody by its Fc receptors onto cells in these organs.

A second example would be binding of mannose present in the ricin of antibody-ricin conjugate to mannose receptors on liver cells.

Specific antibody: Antibody that binds to epitope on desired target cells through its antigen-recognition sites. Specific antibodies may also bind to epitope or structural homolog present on non-target cells.

Irrelevant antibody: Antibody that does not bind to target cells by means of its antigen-recognition sites, but may bind to non-target and target cells through non-specific mechanisms, e.g., Fc portion of antibody binding to Fc receptors on cells in reticuloendothelial system (RES).

Blocking antibody: Antibody that inhibits the non-specific binding of pharmaceutically active specific antibody. Blocking antibodies may include irrelevant antibody or pharmaceutically inactive specific antibody or fragments or combinations thereof. The latter may also be called "cold-specific" antibody.

Pharmaceutically active antibody: Anbtibody that is diagnostically or therapeutically effective.

The use of antibodies as carriers for radionuclides and cytotoxins has been a goal of cancer diagnosis and treatment since Pressman et al. showed that 131$_I$labeled rabbit anti-rat kidney antibodies localized in the kidney after intravenous injection (Pressman, D., Keighly, G. (1948) *J. Immunol.* 59:141–46). Just a few years later, Vial and Callahan reported a dramatic, complete response in a patient with widely metastatic malignant melamoma treated with $^{131}$I-antibodies raised against his own tumor (Vial, A. B. and Callahan, W. (1956), *Univ. Mich. Med. Bull.* 20: 284–86). In the 1960s, Bale and co-workers demonstrated that labeled antibodies to fibrin, which is often deposited in rapidly growing tumors, could localize in rat, dog and human tumors (65% of 141 patients) (Bale, W. F., et al. (1960) *Cancer Res.* 20:1501–1504 (1960); McCradle, R. J., Harper, P. V., Spar, I. L., et al. (1966) *J. Nucl. Med.* 7:837–44; Spar, I. L., Bale, W. F., Manack, D., et al. (1969) *Cancer* 78:731–59; Bale, W. F., Centreras, M. A., Goody, E. D. (1980) *Cancer Res.* 40:3965-2972). Several years later, Chao et al. demonstrated selective uptake of antibody fragments in tumors (Chao, H. F., Peiper, S. C., Philpott, G. W., et al. (1974) *Res. Comm. in Chem. Path. & Pharm.* 9:749–61).

Monoclonal antibodies (Kohler, G. and Milstein, C. (1975) *Nature* 256:495–97) offer advantages over the polyclonals used in these studies because of their improved specificity, purity and consistency among lots. These factors, plus their wide availability, have led to improved clinical applications of antibodies and their conjugates.

Even with monoclonals, however, most antibodies to human tumors have some normal tissue cross-reactivity. Compared to tumors, these cross-reactive sites may equally or preferentially bind injected antibody or conjugate and thus adsorb a substantial portion of the administered dose, especially if these sites are concentrated in well-perfused organs. If the antibody is conjugated to a toxic agent, there may be toxicity to the normal tissues that could be dose-limiting. Therefore, reducing normal tissue binding of the antibody or conjugates without adversely affecting their tumor localization would be advantageous.

Also needed in the art are methods to improve the targeting of immunoconjugates to tumor cells. Most immunoconjugates are produced by chemically linking an antibody to another agent. Another possibility is creating a fusion protein. The antibody itself, the process of linking, or the conjugated agent itself may cause decreased locatization to the tumor due to nonspecific or cross-reactive binding.

Also needed in the art is a method to improve delivery of cytotoxins or biologic response modifiers (BRMs) to tumors using antibodies as carriers, while minimizing toxicity.

Also needed in the art are similar methods to improve delivery of cytotoxins or biologic response modifiers (BRMs) to tumors using hormones or other targeting agents as carriers, while minimizing toxicity.

Also needed in the art is a method to decrease formation of antiglobulins to injected antibody or immunoconjugates as there may be inhibition of binding or even toxicity when the same antibody is injected at a later time.

All of these issues can be addressed by the described methods that reduce cross-reactive and nonspecific binding of antibody and antibody conjugates, and are equally applicable to any substance that has a nonspecific uptake site or whose receptors are shared by non-target cells.

The methods of the present invention reduce cross-reaction and/or nonspecific binding of specific antibodies and hormones when administered to diagnose, stage, evaluate or treat diseases such as cancer in humans. The characteristic of specificity makes antibodies potentially useful agents for targeting defined populations of cells such as tumor cells that express tumor-specific (expressed uniquely by tumor cells) or tumor-associated (expressed by tumor cells and by a subpopulation of normal cells) antigens. The clinical utility of these specific antibodies, however, is compromised by the phenomenon of cross-reactive and nonspecific binding.

One method of markedly diminishing nonspecific uptake is to remove a nonspecific binding portion of the antibody, leaving the antigen binding portion [e.g., F(ab)'$_2$, Fab', Fab or Fv]. Fragments may accumulate more rapidly onto the tumor cell than whole antibody due to their smaller size, which facilitates egress from the circulation across blood vessel and capillary walls into the tumor bed. This does not usually compensate for the decreased serum half-life of the fragments resulting in decreased tumor accumulation compared to whole antibody. Thus there exists a need to prolong serum half-life of fragments in order to take advantage of their more rapid accumulation in target cells and, therefore, to improve localization into a tumor. Additionally, nonspecific binding of specific antibodies into normal organs needs to be decreased.

Generally, a major obstacle to the successful clinical use of antibodies and conjugates thereof has been inadequate delivery to target cells. This has been assessed both by immunohistochemistry on frozen sections of tumors removed after antibody administration (Oldham, R. K., Foon, K. A., Morgan, A. C., et al. (1984) *J. of Chem. Oncol.* 2(11):1235–44; Abrams, P. G., Morgan, A. C., Schroff, C. S. (1985) In: *Monoclonal Antibodies and Cancer Therapy* (Deisfeld and Sell, Eds.), Alan R. Liss Inc., pp. 233–36) or by calculating the percent of the radiolabeled antibody dose per gram in the tumor (Murray, J. L., Rosenblum, M. G., Sobol, R. E., et al. (1985) *Cancer Res.* 45: 2376–81; Carrasquillo, J. A., Abrams, P. G., Schroff, R. W., et al. (submitted); Epenetos, A. A., Mather, S., Gwanowska, M., et al. (1982) *Lancet II*:999–1004; Larson, S. M., Carrasquillo, J. A., Krohn, K. A., et al. (1983) *J. Clin. Investigation* 72:2101–2114 (1983). There was clear evidence in the former studies of increased antibody localization in tumor with higher doses of specific antibody. The quantitative studies with radiolabeled antibody have shown 0.0001%–0.0004% of the injected dose/gram localizing to tumor (Carrasquillo, ibid.).

Radiolabeling of antibodies permits the quantitative assessment of percent accretion into tumors and normal organs and disappearance from the blood and the whole body. This serves as a paradigm for the biodistribution and kinetics of antibodies and immunoconjugates. Conjugated or labeled peptides or steroid hormones provide an analogous strategy.

Studies with radiolabeled antibodies have demonstrated that part of the problem causing low tumor accumulation is the localization of radiolabeled antibody in other organs, such as liver, spleen, marrow, lung or kidney. The prior art is replete with examples of increasing mass of specific antibody to improve tumor localization (e.g., Abrams, ibid.; Murray, ibid.; Carrasquillo, ibid.; Epenetos, ibid.; Larson, ibid.). The present invention uses irrelevant antibody to adsorb to these nonspecific sites, thus obviating the requirement for large doses of unconjugated specific antibody required in the prior art. One advantage of this strategy is that unconjugated irrelevant antibody does not compete for specific sites on target cells with conjugated specific antibody. Another advantage is that irrelevant antibody skews the immunological response of the patient away from the specific antibody (vide infra).

One measure of decreased adsorption of specific antibody onto nonspecific sites is prolonged serum half-life of the antibody. Another unexpected result of pre-administering isotype and subclass matched whole irrelevant immunoglobulin is the prolonged serum half-life, reduced nonspecific adsorption and improved tumor detection with fragments of specific antibody.

The prior art recognizes the problem of localizing specific antibody and fragments and conjugates thereof due to nonspecific and cross-reactive binding to non-target epitopes, e.g., Murray, ibid. Yet, the solution employed has been to lump together the problems of nonspecific and cross-reactive uptake and to use a single strategy —— co-administration of large masses of specific unconjugated antibody —— to overcome the problems. The present invention not only distinguishes these problems, but also offers different solutions to each: (1) the use of irrelevant antibody (immunoglobulin) to reduce nonspecific and cross-reactive binding of specific antibody, and (2) the administration of unconjugated specific antibody to bind to cross-reactive sites prior to the administration of conjugated specific antibody. The latter solution applies equally to steroid and piptide hormones.

Since antibodies are proteins, in most cases of non-human origin, the spectre of human antiglobulin and anti-idiotype has been raised (Oldham, ibid.; Abrams, ibid.; Murray, ibid.; Carrasquillo, ibid.; Epenetos, ibid.; Larson, ibid.). This invention demonstrates that the co-administration of larger masses of irrelevant antibody can skew that antiglobulin response toward the irrelevant antibody and not the specific antibody so that, along with either the same or a second irrelevant antibody, the same target-specific antibody can be injected again and localize in tumor sites without significant formation of antiglobulins to the specific antibody.

Despite their increased specifity, monoclonal antibodies thus far have not been entirely tumor-specific, but rather recognize tumor-associated antigens. When their cross-reactivity is predominantly to one organ that can be selectively perfused, the present invention provides methods for targeting specific antibody conjugates by selective direct infusion of unconjugated specific antibody into a vessel feeding a normal organ known to concentrate conjugated antibody by cross-reactive binding. For a therapeutic conjugate, the reduction in toxicity is a substantial advantage.

Conjugates of specific antibody may localize in nonspecific sites due to the molecule linked to the antibody rather than the antibody itself. The protein toxins (e.g., ricin, abrin, diphtheria toxin, pseudomonas toxin) can bind to mammalian cells through particular portions of these molecules. This property has prompted a large effort to eliminate their nonspecific binding capability while preserving the potency of the toxin. According to the methods of the present invention, detoxified protein toxins, when conjugated to nonspecific antibody, can reduce binding of the specific antibody-toxin conjugate to nonspecific sites. This methodology reduces whole organism toxicity and permits the administration of larger doses of the specific toxin conjugate.

DISCLOSURE OF THE INVENTION

The method of the present invention is for enhancement of delivery to target cells of antibodies or fragments thereof or other receptor-mediated delivery systems, such as peptide, specific for a population of cells of a mammal. The method comprises the steps of administering to said mammal an adequate dosage of blocking antibodies or fragments thereof or other receptor-mediated delivery systems, such as peptide, and administering to said mammal an effective dosage of said antibodies or fragments thereof or other agents that target a defined population of cells via receptors, such as hormones, specific for said population of cells, the blocking antibodies or fragments thereof or other targeting agents capable of nonspecific and/or cross-reactive binding to non-target cells. The antibody fragments of either the blocking antibodies or the specific antibodies are selected from the group consisting of F(ab)', F(ab)'$_2$, Fab, Fv and mixtures thereof.

In a preferred embodiment, the target cells are characterized by having tumor-associated antigen. Both the blocking antibodies and the specific antibodies may be either monoclonal or polyclonal antibodies. Furthermore, the specific antibodies and fragments thereof may be conjugated to cytotoxins, radionuclides or biological response modifiers.

The administration of the blocking antibodies is preferably done prior to the administration of the specific antibodies; alternatively, such blocking antibodies may be administered simultaneously with the specific antibody. The effective dosage of the antibodies or fragments thereof specific for a said population of cells is either diagnostically effective or therapeutically effective. The preferred mammal of the methods disclosed herein is man.

An additional preferred embodiment of the methods disclosed herein is for enhancement of the localization of antibodies or fragments thereof specific for a cross-reactive antigen contained within a mammal's tissue or organ. This method comprises the steps of directly perfusing said tissue or organ with an adequate dosage of blocking antibodies or fragments thereof and then administering systemically to the mammal an effective dosage of said antibodies or fragments thereof specific for said antigen contained within said tissue or organ that is also present on target cells.

A related aspect of the present invention discloses a method for reducing within a mammal the production of anti-immunoglobulin directed against antibodies or fragments thereof specific for a population of target cells. This method comprises the steps of administering to said mammal in adequate dosage of blocking antibodies or fragments thereof capable of stimulating the production of anti-immunoglobulin directed against said blocking antibodies or fragments thereof and administering to said mammal a therapeutically effective dosage of said antibodies or fragments thereof specific for said target cells, wherein said therapeutically effective dosage is smaller than said adequate dosage of blocking antibodies or fragments thereof.

BEST MODE FOR CARRYING OUT THE INVENTION

1. Reducing Nonspecific Uptake

An irrelevant antibody may be matched with a specific antibody by species, isotype and/or subclass and is administered, usually in several-fold or greater quantities, to patients prior to the injection of the specific antibody or specific antibody conjugates. Alternatively, such matching may not be necessary. The prior art has demonstrated improved tumor localization of whole antibody with increasing doses of specific antibody. These results were assessed with either trace-labeled specific antibody or by immunohistochemistry following antibody adminstration (Oldham, ibid.; Abrams, ibid.; Murray, ibid.; Carrasquillo, ibid.). In the former, the unlabeled, specific antibody was usually given simultaneously with the labeled preparation. The underlying concept involved providing sufficient mass of antibody to attach to nonspecific sites, leaving more specific antibody available to bind to tumor. There was some reduction of labeled antibody in nonspecific sites (e.g., liver), and a marked increase in serum half-life of the radiolabeled whole immunoglobulin (Carrasquillo, ibid.). There is, however, the potential for competition for specific binding at the tumor site by the labeled and unlabeled antibody. If the label is used symbolically to represent any agent conjugated to antibody, competition of unlabeled antibody for the tumor antigen at the most accessible (perivascular) sites will compromise the delivery of that agent to the tumor. In addition, a percentage of the labeled antibody, when injected simultaneously, behaves as a true tracer and deposits in normal nonspecific and cross-reactived sites.

The method described herein uses irrelevant antibody (blocking antibody) to reduce the nonspecific uptake, without competing for the tumor antigen, preferably administered prior to specific antibody (see Example I). The positive results observed by pre-administering irrelevant antibody were not expected since human gammaglobulins, in large ($>$1 gm) quantities, failed to show any decreased localization of radiolabeled antibody into nonspecific sites (Carrasquillo, ibid.).

Further, the method described herein is applicable to fragments of specific antibody as well as to whole specific antibody. The method also has been shown to increase the serum half-life of fragments.

Particularly unexpected was the prolonged serum half-life in the initial phase of serum clearance achieved by using whole irrelevant antibody prior to specific antibody fragments. This was surprising since it was assumed that the nonspecific binding sites on antibody would be eliminated by creating fragments devoid of the Fc portion of the molecule. This method is useful for reducing non-specific binding of specific antibody, whole or fragment, or conjugates of such antibody, whole or fragment, with radionuclides, drugs, toxins, biologic response modifiers or differentiating agents.

2. Reducing Cross-Reactivity with Normal Tissues

Normal tissues may contain an epitope, or structural homolog of an epitope, expressed on the target cell. Several methods to reduce localization to non-target tissues are presented herein. For normal tissues equally or more accessible than tumors to specific antibody, unconjugated specific antibody (blocking antibody) is administered prior to conjugated specific antibody (see Example II). The antigen sites on normal tissues, such as blood vessels or liver, will first bind the previously injected, unconjugated whole antibody. In one embodiment, the blocking antibody is bivalent (whole or F(ab'$_2$) and the conjugated antibody is monovalent (Fab', Fab or Fv). This approach taken advantage of the higher antigen affinity of the bivalent molecules and thus reduces the competition of the subsequently administered, conjugated monovalent species for the cross-reactive sites.

The precise doses of the cold-specific antibody and the timing of administration will be dependent upon the size of the patient, the quantitative normal tissue expression of the antigen or epitope, the relative accessibility of tumor compared to normal tissue sites, and the purpose for which the entire procedure is being performed. For example, a modest degree of nontumor targeting may be acceptable in a therapeutic study so long as toxicity is tolerable, but less acceptable in an imaging mode where false positives could be a problem.

The dose of the cold-specific antibody can be approximated by administering increasing doses of the cold-specific antibody prior to biodistribution studies with a labeled antibody or labeled conjugate. When normal tissue sites that show evidence of uptake of the radiolabeled antibody or conjugate with no cold-specific antibody are no longer visualized, than an adequate dose of the cold-specific antibody will have been reached. Alternatively, a greater interval may be allowed between the given dose of cold-specific antibody and the subsequent administration of conjugated specific antibody to permit greater permeation of the cold-specific antibody into normal tissues.

Another approach is to determine the serum half-life of an irrelevant antibody or fragment and preadminister sufficient cold-specific antibody or fragment to raise the half-life of the conjugated antibody or fragment close to the half-life of the irrelevant antibody. This would be indirect evidence that a normal tissue antigen "sink" was completely or largely saturated.

An additional method of determining the appropriate dose has been described by Eger et al. Using data obtained from patients receiving the 9.2.27 antibody, they constructed a mathematical model that, by regression analysis, could predict a dose of antibody that would saturate the "antigen sink" in normal tissues.

Once determined for a particular antigen-antibody system, the dose and schedule can be calculated on a body surface area or weight basis for the particular antibody.

Within a wide range, however, the administration of more than a normal tissue saturating dose will have little effect on the delivery of the conjugated antibody to the tumor. The major considerations are saturation of the more accessible tumor sites and affinity differences between unconjugated, "cold" antibody and the conjugate. If the conjugate has substantially less affinity, too large a dose of unconjugated antibody will compete off the conjugate and thus efficacy — therapeutic or detection - will be reduced.

A second method for reducing cross-reactivity with normal tissues that contain the cross-reactive associated antigen involves directed prior or co-administration of unconjugated antibody (see Example III). Generally, venous or arterial access is achieved through percutaneous catheterization. For example, the renal arteries or veins may be catheterized to perfuse the kidneys selectively. Alternatively, a catheter may be placed into an appropriate vessel (e.g., hepatic arttry for liver) at he time of surgery. The unconjugated antibody is injected by the catheter to contact the antigen sites of the normal organ with the "first pass" of antibody. The antibody may be whole or fragmented. Either simultaneously or thereafter, the conjugated antibody is injected into the mammal's general circulation. Binding of the specific conjugated antibody to the previously perfused sites in the normal organs is reduced, thus increasing the availability of the conjugated specific antibody for the target cells. This also results in reduced toxicity to the cross-reactive, non-target organ by the specific conjugated antibody.

A third method involves either peripheral vein or directed infusion as described above. Instead of using unconjugated antibody as the blocking antibody, a conjugate of antibody and detoxified cytotoxin or BRM is infused where the detoxification (i.e., reduced toxicity) process preserves the sites of recognition and/or binding by normal cells (see Example IV). In a preferred embodiment, the detoxified agent is either free or bound to the nonspecific antibody, and the detoxified conjugate is injected prior to the administration of specific antibody conjugate and, if necessary, may be administered as a constant infusion.

In another method, where the tumor to be treated is localized in an organ or a limb, conjugated antibody is injected via directed catheter into the organ or limb following peripheral blockage of cross-reactive and nonspecific sites with unconjugated specific and/or deeoxified, conjugated irrelevant and/or unconjugated irrelevant antibody.

An additional method provides for injection of unconjugated specific antibody via catheter or other means of directing the first administration of the antibody to a defined organ that contains the cross-reactive antigen where the tumor to be treated is disseminated outside of the organ. Unconjugated irrelevant antibody and/or detoxified, conjugated, nonspecific antibody are injected by peripheral vein. Conjugated specific antibody is then injected intraveneously.

3. Reducing Antiglobulin Responses Directed at the Specific Antibody

Irrelevant antibody is administered prior to or simultaneously with specific antibody or specific antibody conjugate. The irrelevant antibody may be administered in higher doses than the specific antibody. In one preferred embodiment, the irrelevant antibody is whole immunoglobulin and the specific antibody is an antibody fragment (see Example V). In another preferred embodiment, the ratio of specific to nonspecific antibody ranges from about 1:1 to about 1:100 and is preferably 1:5. In another preferred embodiment, the nonspecific antibody is whole immunoglobulin and the specific antibody is Fab or Fv. The basis for this strategy is that the higher dose and use of whole, not fragment, of the irrelevant antibody is more likely to evoke an immunological response than the lower dose and less immunogenic fragments of specific antibody.

When a patient develops antiglobulins that bind to the irrelevant antibody but not the specific antibody, the same irrelevant antibody may be administered in a subsequent dose ahead of specific antibody to adsorb the circulating antiglobulin and in higher doses to block nonspecific sites in normal tissues. Any antiglobulins to irrelevant antibody that cross-react with specific antibody would be complexed and deposited in the kidney or reticuloendothelial system, depending on the size of the complex. Most importantly, conjugated specific antibody given subsequently would not be complexed, but would be free to bind to target cells. Alternatively, a second irrelevant antibody that is not recognized by the antiglobulin response may be substituted in subsequent injections. A combination of irrelevant antibodies may also be used.

EXAMPLES

I. Reducing Nonspecific Uptake

Monoclonal antibody (Mab) NR-2AD is a murine IgG$_{2a}$ immunoglobulin that was designed as an anti-idiotype that bound to a single patient's B-cell lymphoma and to no other human tissue. MAb 9.2.27 is a murine IgG$_{2a}$ antibody that recognizes the 250 Kilodalton glycoprotein/proteoglycan melanoma-associated antigen. Both were scaled up by in vitro cell culture, purified by column chromatography, and tested for purity and sterility to meet the draft guidelines for injectable monoclonal antibodies from the Office of Biologics, Food & Drug Administration ("Points to consider in the manufacture of injectable monoclonal antibody products intended for human use in vivo: Revised draft of 6/11/84"). MAb 9.2.27 was digested with pepsin and the F(ab')$_2$ fragment purified from residual intact antibody.

NR-2AD 50 mg was diluted in normal saline and injected intravenously into patient 8501.08 who had metastatic malignant melanoma. One hour later, 2.5 mg Tc-99 m labeled 9.2.27 F(ab')$_2$ was administered intravenously. The patient's blood was withdrawn and counted with a Tc-99 m standard. Surprisingly, the serum half-life (t½) of the labeled F(ab')$_2$ was 17 hours. The average serum t½ of the labeled 9.2.27 F(ab')$_2$ for patients receiving NR-2AD was 12 hours compared to 6 hours for those who did not receive NR-2AD prior to the labeled fragment. The patient's tumor was visualized by gamma camera imaging and then excised. Another unexpected result was the detection of a tumor that weighed only 0.25 gm.

II. Reducing Cross-Reactive Binding of Specific Antibody Conjugates

A. Cold-specific antibody blocks uptake of conjugated specific antibody in normal organs The effect of reducing cross-reactive uptake of a radiolabeled monoclonal antibody preparation was assessed in the context of a diagnostic imaging clinical trial. The patient (#8501.22) examined in the study was a 32-year-old male with a metastatic melanoma lesion in the left posterior portion of the neck. The lesion consisted of a tumorinvolved lymph node measuring 2×2 cm.

The patient received two schedules of radiolabeled antibody three days apart. The first schedule of antibody consisted of two doses: a 50 mg dose of non-radiolabeled intact irrelevant antibody (NR-2AD) administered intravenously followed 1 hour later by a 2.5 mg dose of Tc-99 m radiolabeled Fab fragment of a MAb 9.2.27. The localization of radiolabel within the patient was assessed by gamma camera imaging over a 7 hour period. The second schedule was identical, except that 7.5 mg of non-radiolabeled F(ab')$_2$ fragment of 9.2.27 was administered 5 minutes prior to the radiolabeled Fab preparation. The 50 mg dose of intact irrelevant antibody was administered in both schedules, in order to reduce nonspecific uptake of the radiolabeled antibody into normal tissues. The non-radiolabeled target specific F(ab')$_2$ preparation was administered for the purpose of reducing cross-reactive uptake of the radiolabeled antibody by non-target tissues.

The results of the study showed that omission of the non-radiolabeled target-specific antibody (9.2.27 F(ab')$_2$ was accompanied at 7 hours post-infusion by uptake of radiolabeled antibody into non-target tissue, specifically spleen, bone marrow and kidney. The known tumor site was not imaged. Pre-infusion of the non-radiolabeled target-specific antibody (9.2.27 F(ab')$_2$ was accompanied at the same time point by uptake in the kidney, but no demonstrable uptake in the spleen, bone marrow or other normal organs. This result was unexpected since the marrow and spleen uptake had previously been assumed to be nonspecific. In addition, the known tumor in the neck was clearly visible, confirming that blocking cross-reactive binding sites by prior infusion of non-radiolabeled target-specific antibody both reduced non-target tissue localization and increased tumor localization of the radiolabeled target-specific antibody.

B. Cold-Specific Antibody Blocks Uptake of the Labeled Specific Antibody by an Epitope-Specific Mechanism Patient 8501.29 was a 49-year-old Caucasian male who presented with melanoma on his back that then spread to lymph nodes under his arm. At the time of imaging with the 99 m$_{Tc}$-labeled antibodies, the patient had presumed disease in the right axilla (recurrent), questionable small subcutaneous metastases on his arm and back, and diffuse hepatic involvement, as evidenced by CT scan and elevated hepatic transaminases.

The purpose of the test in this patient was to determine if the cold-specific antibody blocked normal tissue accumulation of the labeled antibody in an antigen-binding site (i.e., epitope-specific) manner. Two antibodies, NR-ML-05 and 9.2.27, that each recognized distinct epitopes of the 250 Kd. glycoprotein/proteoglycan melanomaassociated antigen were chosen for this study.

For the first procedure, the patient received irrelevant antibody NR-2AD (NRX 900.00), cold-specific 9.2.27 (NRX-112), and then radiolabeled NR-ML-05 (NRX 118.03) so that the cold-specific blocker and the labeled antibody recognized distinct epitopes of the same antigen. Gamma camera imaging 4 and 8 hours after injection revealed hepatic metastases, an axillary chain of nodes, but also images of marrow (sternum and pelvis) and spleen. A repeat procedure was identical but substituted NR-ML-05 (NRX 118) as the cold-specific blocker for the 9.2.27 used in the first procedure. Gamma camera imaging revealed the same sites of disease, but this time with the absence of marrow (sternum and pelvis) and splenic uptake of the label.

This example, using the same patient as his own control, demonstrated conclusively that the cold-specific antibody blocked uptake of the labeled specific antibody into normal organs in an epitope-specific manner.

III. Directed Infusion to Reduce Cross-Reactive Binding

Percutaneous catheterization of the celiac and/or pancreatoduodenal arteries is performed through the femoral artery. MAb NR-CO-1 that reacts with colon carcinoma and cross-reacts with normal pancreas is labeled with Tc-99 m. Unlabeled NR-CO-1 F(ab)'$_2$ fragments (10 mg) are injected by 10 minute infusion through the catheter followed by a normal saline flush (directed infusion). At the end of the directed infusion, the labeled NR-CO-1 (2.5 mg) is injected by peripheral vein. Omitting the directed infusion results in increased localization in the pancreas of the subsequently administered, labeled antibody, indicating that the directed infusion can selectively reduce binding of conjugates in organs containing cross-reactive antigen.

IV. Reducing Nonspecific Binding of Conjugates

Pseudomonas exotoxin (PE) and diphtheria toxin (DT) are bacterial proteins that interfere with protein synthesis in cells by ADP-ribosylation of elongation factor-2 (EF-2). DT binds to nicotinamide at glutamic acid in position 148 in the molecule. Substitution of aspartic acid in this position ($DT_{ASP}$) reduces the activity of $DT$ to 1% of the native molecule, but does not affect its binding to cells. PE is thought to have a "pocket" for binding to its substrate that contains a tyrosine (position 481) and glutamic acid (position 553). Iodination of tyrosine 481 ($PE_{tyrI}$) is expected to result in >50% loss in activity of PE ($PE_{tyrI}$) but retention of its binding ability.

NR-2AD (irrelevant immunoglobulin) is reacted with 25 mM dithiothreitol and $PE_{tyrI}$ or $DT_{ASP}$ with SMPB [succinimidyl(4-p-maleimidophenyl) butyrate], and the unreacted reagents are removed. The derivatized antibody and toxin are mixed together, producing NR-2AD-S-C-$PE_{tyrI}$ or NR-2AD-S-C-$DT_{ASP}$ (detoxified conjugates) that are purified by column chromatography. 20-500 mg of the detoxified conjugates is administered intraveneously prior to administration of NR-ML-05-S-C-PE or NR-ML-05-S-C-DT (specific toxin conjugates). NR-ML-05 is a murine monoclonal antibody that recognizes a 250 kilodalton glycoprotein/proteoglycan human melanoma-associated antigen.

The prior administration of the detoxified conjugates is expected to reduce specific conjugate binding in normal nonspecific sites (nonspecific has two components in this example, viz, the nonspecific binding of the irrelevant immunoglobulin part of the conjugate and the nonspecific binding of the modified toxin). The specific toxin conjugate is then injected intravenously in doses two times or greater than could be given without the blockade of non-specific sites with detoxified conjugates. Additionally, unconjugated NR-2AD and unconjugated NR-ML-05 are given prior to the specific toxin conjugates. These methods permit the administration of higher doses of potent immunoconjugate for increased localization and improved tumor reduction.

V. Reducing Antiglobulin Response Directed at a Specific Antibody

The effect of co-administration of an irrelevant monoclonal antibody (NR-2AD) on subsequent antiglobulin development to a specific MAb (9.2.27) was assessed in the context of a diagnostic imaging trail. Sixteen patients with metastatic malignant melanoma received 1 to 25 mg doses of Tc-99 m radiolabeled 9.2.27 monoclonal antibody or fragments thereof, preceded by 5 minutes by doses of 7.5 to 9 mg of non-radiolabeled 9.2.27 or fragments thereof. Thus, patients received total doses of 10 mg of the 9.2.27 antibody and its fragments. One hour prior to administration of the specific antibody, 50 mg doses of a non-radiolabeled intact irrelevant antibody (NR-2AD) was administered to 11 of the 16 patients.

Serologic evidence of an antiglobulin response was evaluated using a solid-phase, enzyme-linked immunoassay (ELISA) employing either the target-specific (9.2.27) or irrelevant (NR-2AD) antibody as the capture antigen. Serum specimens were evaluated from time points ranging from 2 weeks to over 6 months following treatment. Six of the eleven patients evaluated receiving NR-2AD demonstrated evidence of an antiglobulin response to the irrelevant NR-2AD antibody of greater magnitude than that which was obtained in the upper 95th percentile of 60 healthy controls. In the same group of eleven patients, only one person demonstrated an antiglobulin response to the target-specific 9.2.27 antibody above the 95th percentile of the healthy control population.

These data indicate that prior administration of a 5-fold excess of an irrelevant MAb preparation resulted in antiglobulin responses, in those individuals who developed an antiglobulin response, which was skewed toward the irrelevant rather than the target-specific MAb.

VI. Repeated Administration of Antibody in the Presence of Antiglobulins

Patient #8501.08 in the 99 $m_{Tc}$ imaging trail of melanoma received two imaging procedures within a one-week period with the 9.2.27 melanoma-specific antibody and the NR-2AD irrelevant antibody. The patient returned after 8 months and was repeat imaged with the NR-ML-05 melanomaspecific antibody and the NR-2AD antibody. At that time, the patient had developed a 19-fold increase in antiglobulin directed to the NR-2AD antibody. After premedication with 50 mg diphenhydramine, the patient received NR-2AD 41 mg diluted in normal saline slowly over 60 minutes. He then received 10 mg NR-ML-05 cold-specific antibody followed by NR-ML-05 Fab labeled with 99 $m_{Tc}$. The labeled antibody showed no evidence of altered biodistribution and successfully targeted known subcutaneous and liver tumors.

By contrast, studies in normal guinea pigs immunized with murine monoclonal antibodies and imaged with either the same or an irrelevant $^{99\,m}$Tc-labeled antibody demonstrated that the presence of specific antiglobulin altered biodistribution of labeled antibody. Administration of a radiolabeled antibody to which antiglobulin was reactive resulted in biodistribution of the radiolabel to liver and spleen. If the circulating antiglobulin was not specific for the radiolabeled antibody, then biodistribution was indistinguishable from biodistribution in the non-immunized animal.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of enhancing delivery to solid tumor target cells within a mammal of conjugated specific antibodies or fragments thereof pharmaceutically active and specific for said target cells, comprising the steps of:
   administering to said mammal an adequate dosage of blocking antibodies or fragments thereof, said blocking antibodies being capable of blocking the binding of the conjugated specific antibodies or fragments thereof to non-target tissue(s) through antigen recognition; and then
   administering to said mammal a diagnostically or therapeutically effective dosage of said conjugated specific antibodies or fragments thereof, said conjugated specific antibodies being specific for said solid tumor target cells.

2. The method of claim 1 wherein said blocking antibodies or fragments thereof are capable of cross-reactive, epitope-specific binding to non-target cells.

3. The method of claim 1 wherein said antibody fragments are selected from the group consisting of F(ab)', F(ab)'$_2$, Fab, Fv, and mixtures thereof.

4. The method of claim 1 wherein said solid tumor target cells are characterized by having tumor-associated antigen.

5. The method of claim 1 wherein any of the antibodies are monoclonal antibodies.

6. The method of claim 1 wherein any of the antibodies are polyclonal antibodies.

7. The method of claim 1 wherein the conjugated specific antibodies comprise antibodies or fragments thereof specific for said target cells conjugated to a cytotoxin.

8. The method of claim 1 wherein the conjugated specific antibodies comprise antibodies or fragments thereof specific for said target cells conjugated to a radionuclide.

9. The method of claim 1 wherein the effective dosage of conjugated specific antibodies or fragments thereof is diagnostically effective.

10. The method of claim 1 wherein the effective dosage of conjugated specific antibodies or fragments thereof is therapeutically effective.

11. The method of claim 1 wherein the mammal is a human.

12. A method of enhancing the localization at a solid tumor target site of conjugated specific antibodies or fragments thereof specific for an antigen contained on the target site and also on a non-target tissue or organ within a mammal, comprising the steps of:
   perfusing said non-target tissue or organ with an adequate dosage of blocking antibodies or fragments thereof, said blocking antibodies being capable of blocking the binding of the conjugated specific antibodies or fragments thereof to non-target tissue(s) or organ through antigen recognition; and
   administering to the mammal a diagnostically or therapeutically effective dosage of said conjugated specific antibodies or fragments thereof specific for said antigen.

13. The method of claim 12 wherein said blocking antibodies or fragments thereof are capable of cross-reactive, epitope-specific binding to the non-target tissue or organ.

14. The method of claim 12 wherein said antibody fragments are selected from the group consisting of F(ab)', F(ab)'$_2$, Fab, Fv, and mixtures thereof.

15. The method of claim 12 wherein said tissue or organ is characterized by having tumor-associated antigen.

16. The method of claim 12 wherein the antibodies are monoclonal antibodies.

17. The method of claim 12 wherein the antibodies are polyclonal antibodies.

18. The method of claim 12 wherein the conjugated specific antibodies comprise antibodies or fragments thereof conjugated to a cytotoxin or drug.

19. The method of claim 12 wherein the conjugated specific antibodies comprise antibodies or fragments thereof conjugated to a radionuclide.

20. The method of claim 12 wherein the blocking antibodies or fragments thereof and the conjugated specific antibodies or fragments thereof are administered simultaneously.

21. The method of claim 12 wherein the blocking antibodies or fragments thereof are administered prior to the conjugated specific antibodies or fragments thereof.

22. The method of claim 12 wherein the effective dosage of said conjugated specific antibodies or fragments thereof is diagnostically effective.

23. The method of claim 12 wherein the effective dosage of said conjugated specific antibodies or fragments thereof is therapeutically effective.

24. The method of claim 12 wherein the mammal is a human.

25. A method of targeting melanoma in humans, comprising the steps of:
   administering to said human an adequate dosage of unlabeled specific antibody or fragment thereof that binds to a melanoma-associated antigen; and then
   administering to said human a diagnostically or therapeutically effective dose of labeled specific antibody or fragment thereof that binds to the same epitope of the melanoma-associated antigen as the unlabeled specific antibody.

26. The method of claim 25 wherein the antibody or fragment thereof that binds to a melanoma-associated antigen recognizes the 250 Kd. glycoprotein/proteoglycan.

27. The method of claim 25 wherein the antigen-binding region of the antibody or fragment thereof is selected from the group consisting of antigen-binding regions of antibodies 9.2.27 and NR-ML-05, and their clones, chimaeras and derivatives.

28. The method of claim 25 wherein the antigen-binding region of the antibody or fragment thereof recognizes the G$_{D3}$ glycolipid melanoma-associated antigen.

29. The method of claim 25 wherein the antigen-binding region of antibody or fragment thereof recognizes the P97 melamona-associated antigen.

30. A method of enhancing delivery to solid tumor target cells within a mammal of conjugated specific antibodies or fragments thereof pharmaceutically active and specific for said target cells, comprising the steps of:
   administering to said mammal an adequate dosage of blocking antibodies or fragments thereof, wherein said blocking antibodies are the unconjugated form of the conjugated specific antibodies or fragments thereof; and then administering to said mammal a diagnostically or therapeutically effective dosage of said conjugated specific antibodies or fragments thereof, said conjugated specific antibodies being specific for said solid tumor target cells.

31. The method of claim 30 wherein the conjugated specific antibodies comprise antibodies or fragments thereof specific for said target cells conjugated to a radionuclide.

* * * * *